(12) United States Patent
Kees

(10) Patent No.: US 6,281,234 B1
(45) Date of Patent: Aug. 28, 2001

(54) (2-ACYLAMINOTHIAZOLE-4-YL)ACETIC ACID DERIVATIVE

(75) Inventor: Kenneth L. Kees, Glenmoore, PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/307,919

(22) Filed: May 10, 1999

Related U.S. Application Data

(60) Provisional application No. 60/112,008, filed on May 12, 1998.

(51) Int. Cl.$^7$ .................................................. A61K 31/425
(52) U.S. Cl. ......................... 514/365; 514/369; 514/370; 514/371
(58) Field of Search ..................................... 514/365, 369, 514/370, 371

(56) References Cited

U.S. PATENT DOCUMENTS 5,688,821   11/1997   Kees ..................................... 514/371

OTHER PUBLICATIONS

Toth, I., Liebigs Ann. Chem., 1994, pp. 685–688.

Primary Examiner—Theodore J. Criares
Assistant Examiner—Jennifer Kim

(74) Attorney, Agent, or Firm—Arnold S. Milowsky

(57) ABSTRACT

This invention provides compounds of Formula I having the structure

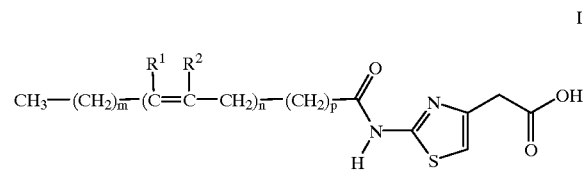

wherein $R^1$, $R^2$ are both hydrogen or form a bond, or are each, independently, alkyl of 1–6 carbon atoms or aryl of 6–12 carbon atoms;

m=0–10;

n=1–3; and p=0–10;

with the proviso that m+p is less than or equal to 15;

or a pharmaceutically acceptable salt thereof, which are useful in treating metabolic disorders related to insulin resistance or hyperglycemia.

9 Claims, No Drawings

(2-ACYLAMINOTHIAZOLE-4-YL)ACETIC ACID DERIVATIVE

This application claims the benefit of U.S. Provisional Application No. 60/112,008, which was converted from U.S. patent application Ser. No. 09/076,708, filed May 12, 1998 now abandoned, pursuant to a petition filed under 37 C.F.R. 1.53(c)(2)(i) on Jun. 16, 1998.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989, 5, 547; Harris et al, Mortality from diabetes, in *Diabetes in America* 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, *Receptor* 1993, 3, 1–15,; F. Ahmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion filled to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism*, 44, 1074, 1995) observed similar increased PTPase activity in the livers of obese, diabetic ob/ob mice, a genetic rodent model of NIDDM.

2-Aminothiazoleacetic acid derivatives have been used extensively in chemical and patent literature as intermediates for penam and cepham classes of antibiotics, but the long ($C_{16}$, $C_{18}$) unsaturated carboxamide chains at $C_2$ of the thiazoleacetic acid moiety makes these compounds novel. WO 9616650 and JP 07149745 generically claim "lower alkyl" amides of 2-aminothiazoleacetic acid are antibacterial and antiinflammatory (elastase inhibitors) agents, respectively. U.S. Pat. No. 5,688,821 (1997, to AHP) teaches that some of the same compounds that are in this invention are inhibitors of the enzymes phospholipase $A_2$ derived from human sources (anti-inflammatory agents), but others are not and vice-versa. Certain long acylhydrocarbon chain derivatives of 2-aminothiazoleacetic acid have been prepared (Toth, *Liebigs Ann. Chem. EN*, 7, 685, 1994).

DESCRIPTION OF THE INVENTION

The compounds of this invention have been shown to inhibit rat-derived and human derived recombinant PTPase-1B (rPTP-1B) in vitro. They are useful in the treatment of insulin resistance associated with obesity, glucose intolerance, diabetes mellitus, hypertension and ischemic diseases of the large and small blood vessels.

This invention provides a method of using a compound of formula I having the structure

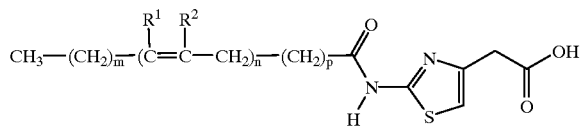

I wherein
R$^1$, R$^2$ are both hydrogen or form a bond, or are each, independently, alkyl of 1–6 carbon atoms or aryl of 6–12 carbon atoms;
m=0–10;
n=1–3; and
p=0–10;
with the proviso that m+p is less than or equal to 15; or a pharmaceutically acceptable salt thereof in the treatment of metabolic disorders related to insulin resistance or hyperglycemia, primary hypertension, or atherosclerosis.

Pharmaceutically acceptable salts can be formed from organic and inorganic bases, such as alkali metals (sodium, potassium, or lithium), alkaline earth metals (calcium or magnesium), ammonium, primary, secondary alkyl amines, or tertiary alkyl amines. The use of tromethamine salts of the compounds of this invention showed improved water solubility and bioavailability.

It is understood that the compounds of this invention can exhibit E (trans) or Z (cis) stereoisomerism about the double bond, and that this invention covers both the E and Z isomers, at each double bond, and in particular when R$^1$ and R$^2$ are both hydrogen, alkyl, or aryl. When R$^1$ and R$^2$ are not a bond, it is preferred that they both are hydrogen.

Preferred compounds of this invention are those in which:
m=1 and n=3 and p=6;
m=4 and n=3 and p=3;
m=5 and n=1 and p=6 or 8;
m=7 and n=1 and p=6; and
m=10 and n=1 and p=3.

Aryl is defined as an organic radical derived from an aromatic hydrocarbon by the removal of a hydrogen (i.e., phenyl from benzene). It is preferred that the aryl moiety is a phenyl or naphthyl group; with phenyl being most preferred. The aryl moiety may be optionally mono-, di-, or tri-substituted with a substituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —CO$_2$H, alkylcarbonyloxy of 2–7 carbon atoms, and alkylcarbonyl of 2–7 carbon atoms.

The compounds of this invention can be synthesized by saponification of the corresponding 2-fatty acylaminothiazole-4-acetic acid ethyl esters, followed by acidification of the reaction mixture. Basic salts of these acids are prepared also in a conventional manner as is known in the art. In particular the tromethamine salts of this invention provide water soluble derivatives for improved bioavailability. The fatty acylaminothiazoleacetic acid esters are prepared in one of two ways: condensation of ethyl-2-aminothiazoleacetate with a fatty acid chloride in the presence of a tertiary amine base such as triethylamine or diisopropylethylamine in an aprotic solvent (e.g. dichloromethane or tetrahydrofuran) at ice temperature (Procedure A) or, preferably, directly from the fatty acid with the aid of an organodiimide coupling agent as is well known in the synthesis of peptides (Procedure B). The fatty acyl starting materials are either prepared according to standard chemical methodology (such as Wittig or Peterson olefination reactions and or modifications thereof, or by reductive dicarbonyl coupling reactions, such as those procedures of McMurry, Corey and Mukiyama), or from commercially available starting materials General procedures to prepare representative compounds of this invention are disclosed in U.S. Pat. No. 5,688,821, which is hereby incorporated by reference, and the preparation of specific representative compounds of this invention are provided in Examples which follow.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes. Additionally, because an association exists between insulin resistance and hypertension and between insulin resistance, hypertension and coronary artery disease, the compounds of this invention are also useful for the treatment of primary (essential) hypertension and atherosclerosis.

The ability of compounds of this invention to treat or inhibit disorders related to insulin resistance or hyperglycemia was established with representative compounds of this invention in the following pharmacological test procedures which measure the inhibition of PTPase.

Inhibition of Recombinant Rat Protein Tyrosine Phosphatase 1B (rPTP1B) Activity Using p-nitrophenylphosphate as a Substrate.
Measurement of pNPPase Activity.

The assay is conducted as described by Moss (Acid Phosphatases. In: Methods of Enzymatic Analysis, Enzymes 2: Esterases, Glycosidases, Lyases, Ligases. Bergmeyer, H. U., ed. Weinheim: Verlag Chemie GmBH, 1984: 92) and Tonks, et al., *J. Biol. Chem.* 263, 6731, 1988), with minor modifications. The incubation mixture contains in a final volume of 0.24 ml: 50 mM HEPES (pH 7.4), 6.33 mM p-nitrophenyl phosphate and 5/25/100 μM compound suspended in 1.25% DMSO. rPTP1B (obtained from the laboratory of Dr. Barry Goldstein of Thomas Jefferson University. The enzyme (see Goldstein et al. *Mol. Cell. Biochem.* 109, 107, 1992), in microvials containing 500–700 μg/ml protein in 33 mM TRIS-HCl, 2 mM EDTA, 10% glycerol and 10 mM 2-mercaptoethanol) is preincubated with drug in HEPES buffer for ten minutes at 37° C. The reaction is started by the addition of p-nitrophenyl phosphate and after 30 minutes at 37° C., the reaction is terminated by adding 1 ml of 0.1 N NaOH. The assay is performed in triplicate and the reaction mixture contains approximately 3.3 μg/ml protein, the above components, plus: 5.50 mM TRIS-HCl, 8.33 mM 2-mercaptoethanol, 0.33 mM EDTA and 1.67% glycerol. The samples are read at 410 nm in a spectrophotometer and are evaluated based on a calibration curve of p-nitrophenol standard solution.

Compounds were screened robotically at a single concentration of ~25 μM. The results are expressed as percent of control, in that the amount of p-nitrophenol formed in the compound treated samples (nmol/minute/mg protein) is compared to the amount (nmol/minute/mg protein) formed in the untreated samples. p-Nitrophenylphosphatase activity is also determined in each experiment and is expressed per minute per mg protein. Representative results are given in Table 1.

Inhibition of Recombinant Human Protein Tytosine Phosphatase 1B

A representative compound (Example 8) of this invention was also evaluated for inhibition of recombinant human PTP1B.

Human recombinant PTP1B was prepared as described by Goldstein (see Goldstein et al. *Mol. Cell. Biochem.* 109, 107, 1992). The enzyme preparation used was in microtubes containing 500–700 μg/ml protein in 33 mM Tris-HCl, 2 mM EDTA, 10% glycerol and 10 mM 2-mercaptoethanol.

Measurement of PTPase Activity.

The malachite green-ammonium molybdate method, as described (Lanzetta et al. *Anal. Biochem.* 100, 95, 1979) and adapted for a platereader, is used for the nanomolar detection of liberated phosphate by recombinant PTP1B. The assay uses, as substrate, a dodecaphosphopeptide custom synthesized by AnaSpec, Inc. (San Jose, Calif.). the peptide, TRDIYETDYYRK, corresponding to the 1142–1153 catalytic domain of the insulin receptor, is tyrosine phosphorylated on the 1146, 1150, and 1151 tyrosine residues. The recombinant rPTP1B is diluted with buffer (pH 7.4, containing 33 mM Tris-HCl, 2 mM EDTA and 50 mM b-mercaptoethanol) to obtain an approximate activity of 1000–2000 nmoles/min/mg protein. The diluted enzyme (83.25 mL) is preincubated for 10 min at 37° C. with or without test compound (6.25 mL) and 305.5 mL of the 81.83 mM HEPES reaction buffer, pH 7.4 peptide substrate, 10.5 ml at a final concentration of 50 mM, and is equilibrated to 37° C. in a LABLINE Multi-Blok heater equipped with a titerplate adapter. The preincubated recombinant enzyme preparation (39.5 ml) with or without drug is added to initiate the dephosphorylation reaction, which proceeds at 37° C. for 30 min. The reaction is terminated by the addition of 200 mL of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 mL MG/AM/Tw to substrate and followed by 39.5 ml of the preincubated recombinant enzyme with or without drug. The color is allowed to develop at room temperature for 30 min. and the sample absorbances are determined at 650 nm using a platereader (Molecular Devices). Sample and blanks are prepared in quadruplicates.

PTPase activities, based on a potassium phosphate standard curve, are expressed as nmoles of phosphate released/min/mg protein. Inhibition of recombinant PTP1B by test compounds is calculated as percent of phosphatase control. A four parameter non-linear logistic regression of PTPase activities using SAS release 6.08, PROC NLIN, is used for determining $IC_{50}$ values of test compounds. Representative results are given in Table 2.

TABLE 1

Inhibition of recombinant phosphotyrosine phosphatase 1B by compounds of this invention.

| Example | % inhibition[a] |
|---|---|
| 1 | 93.4 |
| 2 | 93.9 |
| 3 | 58.16 |
| 4 | 84.8 |
| 5 | 94.97 |
| 6 | 93.77 |

TABLE 1-continued

Inhibition of recombinant phosphotyrosine phosphatase 1B by compounds of this invention.

| Example | % inhibition[a] |
|---|---|
| 7 | 83.8 |
| 8 | 96.6 |
| 9 | 92.4 |
| $(NH_4)Mo_7O_{24} \cdot 4 H_2O$ | 92.3 |
| $Na_3VO_4$ | 86.3 |

[a]All compounds administered at 25 μM

TABLE 2

Dose-response inhibition data and $IC_{50}$ for Example 8 vs rPTP1B (human)

| % inhibition | Dose (μM) |
|---|---|
| 100 | 10 |
| 96.8 | 2.5 |
| 94.94 | 1 |
| 73.21 | 0.5 |
| 43.25 | 0.25 |
| 25.53 | 0.1 |
| $IC_{50}$: | 0.267 |

Based on the results obtained in the standard pharmacological test procedures, representative compounds of this invention have been shown to inhibit PTPase activity, and are therefore useful in treating metabolic disorders related to insulin resistance or associated with obesity or glucose intolerance. More particularly, the compounds of this invention are useful in the treatment or inhibition of type II diabetes, and in modulating glucose levels in disorders such as type I diabetes. The compounds of this invention are also useful in the treatment of primary (essential) hypertension and atherosclerosis. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Compounds of this invention may be administered neat or with a pharmaceutical carrier to a patient in need thereof. The pharmaceutical carrier may be solid or liquid.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1 (Procedure A)

2-[((Z)-1-Oxo-9-octadecenyl)amino]-4-thiazoleacetic Acid

A mixture of ethyl 2-aminothiazoleacetic acid (4.6 g, 24.7 mmol) and triethylamine (4.2 mL, 20.3 mmol) in dichloromethane (125 mL) was cooled in an ice bath under $N_2$ atmosphere. Oleoyl chloride (neat 75%, 11 mL, 25 mmol) was added dropwise and the reaction was then allowed to warm to room temperature. After 15 h at room temperature 10% aqueous HCl solution was added to the reaction mixture, stirred for 2 h and then poured onto saturated aqueous brine solution in a separatory funnel. The organic layer was separated, dried over anhydrous $MgSO_4$, filtered and concentrated on a rotary evaporator to a yellow oil. The crude ester was purified by HPLC (70% hexane, 30% EtOAc) to give 4 g of ethyl-2-[((Z)-1-oxo-9-octadecenyl) amino]-4-thiazoleacetate, as a yellow oil. IR (film) $\mu$ (cm$^{-1}$): 1745, 1700. MS (EI) m/z 450 (M$^+$).

Ethyl-2-[((Z)-1-oxo-9-octadecenyl)amino]-4-thiazoleacetate (4 g, 8.89 mmol), sodium hydroxide (0.79 g, 19.8 mmol) and tetrahydrofuran (50 mL) were combined and cooled in an ice bath under $N_2$ atmosphere. Enough distilled water was added to the mixture to dissolve the hydroxide and provide a homogeneous solution. The reaction was kept at 0° C. for 2 h, then allowed to warm to room temperature and stirred overnight. Aqueous 10% HCl solution was added to the mixture, and stirring continued for 1 h. Ethyl acetate and saturated aqueous brine solution were added to the mixture, and the organic phase was separated and dried over $MgSO_4$. After filtration and concentration the crude dark amber oil was treated with ether, stirred for 0.5 h and the product was collected on a Buchner funnel and air dried to give 1.5 g of the title compound as a white solid, mp 106–108.5° C.

Analysis for: $C_{23}H_{38}N_2O_3S$

Calc'd: C, 65.36; H, 9.06; N, 6.63

Found: C, 64.99; H, 9.19; N, 6.57

EXAMPLE 2 (Procedure B)

2-[((E)-1-Oxo-9-octadecenyl)amino]-4-thiazoleacetic Acid

A mixture of elaidic acid (5.1 g, 17.7 mmol; 98%), ethyl-2-aminothiazoleacetate (3.3 g, 17.7 mmol), triethylamine (2.8 g, 27.7 mmol), 1-(3-dimethylaminopropyl)-3-ethyl carbodiimide hydrochloride (5.3 g, 26.9 mmol) and 4-dimethylaminopyridine (0.4 g, 3.3 mmol) was combined in dichloromethane (225 mL) at ice temperature under $N_2$ atmosphere. The mixture was stirred at 0° C. for 1 h, then allowed to warm to room temperature and stirred for 15 h. The reaction mixture was diluted with water and the organic phase was separated, washed with water and saturated brine solution, dried over $MgSO_4$, filtered and concentrated to give 7.1 g of ethyl-2-[((E)-1-oxo-9-octadecenyl)-amino]-4-thiazoleacetate, which was used directly without purification.

A mixture of the above ester (7.4 g, 16.5 mmol) and sodium hydroxide (1.44 g, 36.1 mmol) was combined in THF (150 mL) and cooled in ice under $N_2$ atmosphere. Enough distilled water was added portionwise until the hydroxide was dissolved (~15 mL) and the mixture was maintained at 0° C. for 2 h, then allowed to warm to ambient temperatures with stirring for 15 h. The reaction mixture was evaporated in vacuo, the residue cooled in ice and treated with 2M aqueous HCl solution with stirring. The white precipitate was collected by vacuum filtration, washed with water and air dried. This material was crystallized from boiling heptane, filtered hot, and dried overnight on an abderhalden apparatus (refluxing acetone) to give 4.6 g of the title compound as a white powder, mp 116–118° C.

Analysis for: $C_{23}H_{38}N_2O_3S$

Calc'd: C, 65.37; H, 9.06; N, 6.63

Found: C, 65.33; H, 9.15; N, 6.59

EXAMPLE 3

2-[((E)-1-Oxo-9-octadecenyl)amino]-4-thiazoleacetic Acid, Tromethamine (2-amino-2-hydroxymethyl)-1,3-propanediol) Salt A mixture of the title compound of Example 2 (3.0 g 7.1 mmol), tris (hydroxymethyl)amino methane (0.86 g, 7.1 mmol) and absolute ethanol (75 mL) were heated on a hot plate until a homogeneous solution was obtained. The solution was allowed to stand at room temperature for several hours and the solvent removed on a rotary evaporator. The residue was slurried in toluene and the solvent removed invacuo. The glassy solid was heated under vacuum at 35° C. for 24 h to give 3.39 g of the title compound, as a white solid, mp 163–164° C.

Analysis for: $C_{27}H_{49}N_3O_6S$

Calc'd: C, 59.64; H, 9.08; N, 7.73

Found: C, 59.46; H, 9.05; N, 7.89

EXAMPLE 4

2-[(1-Oxo-9-octadecenyl)amino]-4-thiazoleacetic Acid

The title compound was prepared by Procedure A (example 1). The crude product was crystallized from hot heptane to give lemon colored crystals, mp 95.5–96.5° C.

Analysis for: $C_{23}H_{36}N_2O_3S$

Calc'd: C, 65.68; H, 8.63; N, 6.66

Found: C, 65.46; H, 8.53; N, 6.74

EXAMPLE 5

2-[((Z)-1-Oxo-6-octadecynyl)amino]-4-thiazoleacetic acid

The title compound was prepared by the method of procedure B (example 2). The crude product was recrystallized from heptane on a steam bath to provide white crystals, mp 104.5–105.5° C.

Analysis for: $C_{23}H_{38}N_2O_3S$; Calc'd: C, 65.37; H, 9.06; N, 6.63; Found: C, 65.45; H, 9.06; N, 6.58.

EXAMPLE 6

2-[((Z)-1-Oxo-9-hexadecenyl)amino]-4-thiazoleacetic Acid

The title compound was prepared by the method of procedure B. The crude product was treated with hot heptane (steam bath) cooled to room temperature and collected on a Buchner funnel. The material was air dried for several hours, then in an Abderhalden apparatus (refluxing acetone) overnight to provide the title compound as a white waxy solid, mp 108–110° C.

Analysis for: $C_{21}H_{34}N_2O_3S$
Calc'd:C, 63.92; H, 8.68; N, 7.10
Found: C, 64.27; H, 8.86; N, 7.32

EXAMPLE 7

2-[((E)-1-Oxo-9-hexadecenyl)amino]-4-thiazoleacetic Acid

The title compound was prepared by the method of procedure B. The crude acid was recrystallized from hot heptane to give the product as white crystals, mp 117–118° C.

Analysis for: $C_{21}$; $H_{34}N_2O_3S$
Calc'd:C, 63.92; H, 8.69; N, 7.10
Found: C, 63.78; H, 8.73; N, 6.79

EXAMPLE 8

2-[((E)-1-Oxo-11-octadecenyl)amino]-4-thiazoleacetic Acid

The title compound was prepared according to the method of procedure B. The crude product was crystallized from hot heptane to give white crystals, mp 115.8–117.1° C.

Analysis for: $C_{23}H_{38}N_2O_3S$
Calc'd: C, 61.99; H, 9.06; N, 6.63
Found: C, 65.74; H, 8.85; N, 6.32

EXAMPLE 9

2-[((Z,Z,Z)-1-Oxo-9,12,15-octadecatrienyl)amino]-4-thiazoleacetic Acid

The title compound was prepared by procedure B and precipitated from heptane as a hygroscopic yellow wax.

Analysis for: $C_{23}H_{34}N_2O_3S \cdot 1.5\ H_2O$
Calc'd: C, 61.99; H, 7.92; N, 6.29
Found: C, 62.22; H, 7.68; N, 6.02

EXAMPLE 10

2-[((Z,Z,Z)-1-Oxo-6,9,12-octatrienyl)amino]-4-thiazoleacetic Acid

The title compound was prepared according to procedure B. The crude product was chromatographed on $SiO_2$ (flash column, 40 wt. eq., elution with hexane (70%), ethyl acetate (30%), acetic acid (1%)) to give the title compound as a pale yellow wax.

Analysis for: $C_{23}H_{34}N_2O_3S$
Calc'd:C, 65.99; H, 8.91; N, 6.69
Found: C, 65.76; H, 8.33; N, 5.50

What is claimed is:

1. A method of treating metabolic disorders mediated by insulin resistance or hyperglycemia in a mammal in need thereof which comprises administering to said mammal, a compound of formula I having the structure

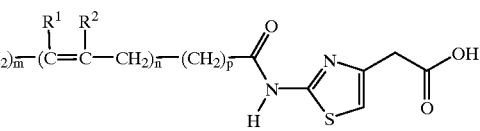

I wherein
$R^1$, $R^2$ are both hydrogen or form a bond, or are each, independently, alkyl of 1–6 carbon atoms or aryl of 6–12 carbon atoms;
m=0–10;
n=1–3; and
p=0–10;
with the proviso that m+p is less than or equal to 15;
or a pharmaceutically acceptable salt thereof.

2. The method according to claim 1, wherein
m=1 and n=3 and p=6;
m=4 and n=3 and p=3;
m=5 and n=1 and p=6 or 8;
m=7 and n=1 and p=6; or
m=10 and n=1 and p=3
or a pharmaceutically acceptable salt thereof.

3. The method according to claim 1, wherein the compound administered is
a) 2-[((Z)-1-oxo-9-octadecenyl)amino]-4-thiazoleacetic acid;
b) 2-[((E)-1-oxo-9-octadecenyl)amino]-4-thiazoleacetic acid;
c) 2-[(1-oxo-9-octadecynyl)amino-]4-thiazoleacetic acid;
d) 2-[((Z)-1-oxo-6-octadecenyl)amino]-4-thiazoleacetic acid;
e) 2-[((Z)-1-oxo-9-hexadecenyl)amino]-4-thiazoleacetic acid;
f) 2-[((E)-1-oxo-9-hexadecenyl)amino]-4-thiazoleacetic acid;
g) 2-[((E)-1-oxo-11-octadecenyl)amino]-4-thiazoleacetic acid; or
h) 2-[((Z,Z,Z)-1-oxo-9,12,15-octadecatrienyl)amino]-4-thiazoleacetic acid or a pharmaceutically acceptable salt thereof.

4. A method of treating or inhibiting type II diabetes in a mammal in need thereof which comprises administering to said mammal, a compound of formula I having the structure

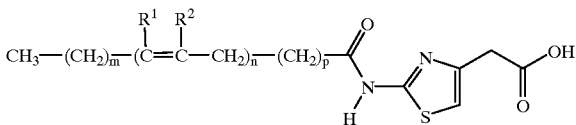

I wherein
$R^1$, $R^2$ are both hydrogen or form a bond, or are each, independently, alkyl of 1–6 carbon atoms or aryl of 6–12 carbon atoms;

m=0–10;

n=1–3; and p=0–10;

with the proviso that m+p is less than or equal to 15; or a pharmaceutically acceptable salt thereof.

5. The method according to claim 4, wherein m=1 and n=3 and p=6;

m=4 and n=3 and p=3;

m=5 and n=1 and p=6 or 8;

m=7 and n=1 and p=6; or m=10 and n=1 and p=3 or a pharmaceutically acceptable salt thereof.

6. The method according to claim 4, wherein the compound administered is a) 2-[((Z)-1-oxo-9-octadecenyl)amino]-4-thiazoleacetic acid;

b) 2-[((E)-1-oxo-9-octadecenyl)amino]-4-thiazoleacetic acid;

c) 2-[(1-oxo-9-octadecynyl)amino]-4-thiazoleacetic acid;

d) 2-[((Z)-1-oxo-6-octadecenyl)amino]-4-thiazoleacetic acid;

e) 2-[((Z)-1-oxo-9-hexadecenyl)amino]-4-thiazoleacetic acid;

f) 2-[((E)-1-oxo-9-hexadecenyl)amino]-4-thiazoleacetic acid;

g) 2-[((E)-1-oxo-11-octadecenyl)amino]-4-thiazoleacetic acid; or h) 2-[((Z,Z,Z)-1-oxo-9,12,15-octadecatrienyl)amino]-4-thiazoleacetic acid or a pharmaceutically acceptable salt thereof.

7. A method of modulating glucose levels in a mammal in need thereof which comprises administering to said mammal, a compound of formula I having the structure

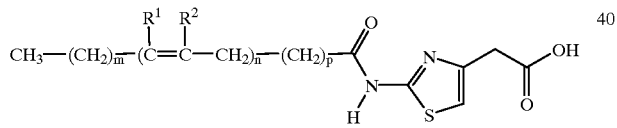

I wherein $R^1$, $R^2$ are both hydrogen or form a bond, or are each, independently, alkyl of 1–6 carbon atoms or aryl of 6–12 carbon atoms;

m=0–10;

n=1–3; and p=0–10;

with the proviso that m+p is less than or equal to 15; or a pharmaceutically acceptable salt thereof.

8. The method according to claim 7, wherein m=1 and n=3 and p=6;

m=4 and n=3 and p=3;

m=5 and n=1 and p=6 or 8;

m=7 and n=1 and p=6; or m=10 and n=1 and p=3 or a pharmaceutically acceptable salt thereof.

9. The method according to claim 8, wherein the compound administered is a) 2-[((Z)-1-oxo-9-octadecenyl)amino]-4-thiazoleacetic acid;

b) 2-[((E)-1-oxo-9-octadecenyl)amino]-4-thiazoleacetic acid;

c) 2-[(1-oxo-9-octadecynyl)amino]-4-thiazoleacetic acid;

d) 2-[((Z)-1-oxo-6-octadecenyl)amino]-4-thiazoleacetic acid;

e) 2-[((Z)-1-oxo-9-hexadecenyl)amino]-4-thiazoleacetic acid;

f) 2-[((E)-1-oxo-9-hexadecenyl)amino]-4-thiazoleacetic acid;

g) 2-[((E)-1-oxo-11-octadecenyl)amino]-4-thiazoleacetic acid; or h) 2-[((Z,Z,Z)-1-oxo-9,12,15-octadecatrienyl)amino]-4-thiazoleacetic acid or a pharmaceutically acceptable salt thereof.

* * * * *